(12) United States Patent
Smith

(10) Patent No.: US 7,969,566 B2
(45) Date of Patent: Jun. 28, 2011

(54) APPARATUS AND METHOD FOR DETECTION OF A FILM ON A SURFACE

(75) Inventor: Becky Smith, Arlington, WA (US)

(73) Assignee: The Boeing Company, Chicago, IL (US)

( * ) Notice: Subject to any disclaimer, the term of this patent is extended or adjusted under 35 U.S.C. 154(b) by 228 days.

(21) Appl. No.: 12/133,804

(22) Filed: Jun. 5, 2008

(65) Prior Publication Data

US 2009/0303488 A1 Dec. 10, 2009

(51) Int. Cl.
*G01N 21/00* (2006.01)
(52) U.S. Cl. .................. 356/237.2; 356/239.8; 340/583
(58) Field of Classification Search .... 356/239.1–239.4, 356/239.7, 239.8, 630–632; 340/583, 962; 244/144

See application file for complete search history.

(56) References Cited

U.S. PATENT DOCUMENTS

| | | | | |
|---|---|---|---|---|
| 3,540,025 A | * | 11/1970 | Bright et al. | 340/583 |
| 4,404,852 A | | 9/1983 | Goto | |
| 5,296,853 A | * | 3/1994 | Federow et al. | 340/962 |
| 5,596,320 A | * | 1/1997 | Barnes | 340/962 |
| 5,748,091 A | * | 5/1998 | Kim | 340/583 |
| 5,883,704 A | * | 3/1999 | Nishi et al. | 355/67 |
| 6,430,996 B1 | * | 8/2002 | Anderson et al. | 73/170.26 |
| 6,467,282 B1 | | 10/2002 | French et al. | |
| 2004/0206854 A1 | * | 10/2004 | Shah et al. | 244/144 |
| 2005/0030529 A1 | * | 2/2005 | Schuler et al. | 356/239.8 |
| 2006/0071151 A1 | * | 4/2006 | Fukamura et al. | 250/214.1 |
| 2007/0001861 A1 | * | 1/2007 | Levine | 340/583 |
| 2007/0114225 A1 | * | 5/2007 | Smith et al. | 219/502 |
| 2007/0216536 A1 | * | 9/2007 | Alfano et al. | 340/583 |

\* cited by examiner

Primary Examiner — Hoa Q Pham

(57) ABSTRACT

An apparatus for detection of the existence of a film on a surface comprises a lens, a light emitter and a light sensor. The light emitter is preferably disposed in spaced relation to the lens and is configured to emit light toward the lens such that the light is incident thereupon. The light sensor is also preferably disposed in spaced relation to the lens and is mounted adjacent to the light emitter. The light sensor is configured to measure light reflected back from the lens. The presence or absence on the film on the surface is based upon the amount (i.e., intensity) of light that is reflected back from the lens. The apparatus may further comprise a temperature sensor or atmospheric sensor for measuring a temperature of the lens and atmospheric conditions in order to determine whether conditions are appropriate for the formation of ice, frost and other frozen contaminants.

18 Claims, 3 Drawing Sheets

APPARATUS AND METHOD FOR DETECTION OF A FILM ON A SURFACE

CROSS-REFERENCE TO RELATED APPLICATIONS (Not Applicable)

STATEMENT RE: FEDERALLY SPONSORED RESEARCH/DEVELOPMENT (Not Applicable)

FIELD

The present invention relates generally to detection of films on surfaces and, more particularly, to an apparatus for detecting the presence or absence of surface contaminants such as snow, frost, ice and insect debris on a surface.

BACKGROUND

The accumulation of frozen contaminants (i.e., frost, snow, ice) and other debris (i.e., dirt, dust, insect residue) on an aircraft can have a significant impact on the safety and operation of the aircraft. Likewise, during wind-tunnel testing, the buildup of frost on aircraft wings can compromise the validity of the test and affect the accuracy of the test results requiring that the frost be removed and testing restarted.

For in-service aircraft such as commercial airliners, the accumulation of frost, snow or ice on the aircraft wings can significantly alter the lift and drag characteristics and can increase stall speed, reduce controllability and alter other flight characteristics. In addition to adding weight to the aircraft, frost and ice formations on wings can increase the surface roughness in critical areas such as on the wing leading edges and upper surfaces and can result in a reduction in lift of up to 30% and an increase in drag of up to 40%.

Ice buildup on control surfaces such as rudders, elevators and ailerons can have a significant impact on aircraft performance and controllability. In addition, the buildup of snow, frost and other types of debris such as insect residue on external instrumentation sensors such as pitot/static ports and angle-of-attack indicators can cause inaccurate readouts of flight instrumentation critical to safe flight.

In-flight aircraft are subject to a variety of atmospheric conditions that can result in accumulations of ice on the aircraft. Factors such as ambient temperature, aircraft surface skin temperature, relative humidity and air speed can influence whether or not ice, frost or snow accumulates. For example, precipitation occurring at ambient temperatures below freezing can remain in a supercooled liquid state (i.e., freezing rain) and can accumulate on the leading edge and upper surfaces of an aircraft wing causing surface roughness which can significantly alter the aircraft flight characteristics.

Parked aircraft and aircraft undergoing ground operations (i.e., taxiing, re-fueling, passenger loading) are also susceptible to accumulations of frozen contaminants. For example, residual ice from a previous flight can remain on wing leading edges and other control surfaces of the aircraft. Under high humidity conditions, frost can accumulate on aircraft during overnight ground storage.

Unfortunately, frost and other ice formations are difficult to detect visually due to the translucent or nearly-translucent nature of such formations. Clear ice is likewise difficult to detect other than by tactile means. Such clear ice can form on the upper surfaces of wings in areas adjacent the fuel tanks of aircraft that have recently landed after high altitude operation. The fuel tanks of such aircraft may contain super-cooled fuel as a result of the high altitude operation and can cause rain, drizzle or high humidity to freeze upon contact with the outer wings surfaces in areas adjacent to the fuel tanks.

In light of the safety issues raised by accumulation of frozen contaminants on aircraft, the Federal Aviation Administration (FAA) implemented a "clean aircraft" concept as currently defined by Federal Aviation Regulations (FAR) for airline operations. In general, the clean aircraft concept prohibits take-off of an aircraft when snow, ice or frost adheres to wings, control surfaces and other components of the aircraft. As part of the clean aircraft concept, FAR regulations require operators to install ground deicing/anti-icing equipment during winter operations. Deice materials typically comprise heated solutions of freezing point depressant (FPD) fluids which are applied to areas of the aircraft suspected of having accumulations of frozen contaminants. Anti-icing fluids are typically thicker and have a lower freezing point in order to provide a protective film for delaying reformation of frozen contaminants.

Despite deicing and anti-icing measures, detection of the accumulation of frozen contaminants such as snow, ice, and frost on an aircraft or other vehicle is difficult. Clear ice is difficult to detect visually regardless of its thickness and may not be detectable other than by tactile inspection by personnel with the use of special equipment such as man-lifts that are required to access wings and control surfaces of larger aircraft. Furthermore, the use of such special equipment presents the potential for damage to the aircraft and injury to personnel under the types of weather conditions that are conducive to the formation of ice.

Because tactile inspection of in-flight aircraft surfaces is impossible and considering the above-described difficulties associated with visual detection of frozen contaminants, it can be seen that there exists a need in the art for a system and method for detecting and warning of the presence or absence of frozen contaminants and other debris (i.e., dirt, dust and insect residue) in order to improve the safety and operation of aircraft and other vehicles and structures. Furthermore, there exists a need in the art for a system and method for detecting the existence of frozen contaminants and other debris on ground-based vehicles such as wind tunnel models in order to reduce the loss of time and expense associated with undetected frost buildup.

Additionally, there exists a need in the art for a system and method for detecting films on surfaces that does not rely on visual or tactile inspection and which has the capability for distinguishing between the composition of the contaminant (i.e., insect debris vs. ice accumulation). Finally, there exists a need in the art for a system and method for detecting films on surfaces which is of low cost, simple in construction and reliable in operation.

SUMMARY

The above-described needs associated with film contamination on surfaces are specifically addressed and alleviated by the embodiments disclosed herein of an apparatus for detecting the presence or absence of a film on a surface such as on an aircraft structure. In its broadest sense, the apparatus may comprise a lens, a light emitter and a light sensor. The combination of a light emitter and the light sensor may form a photoreflective sensor or a photodetector. The photoreflective sensor is preferably disposed in spaced relation to the lens and, more specifically, is preferably disposed adjacent an inner surface of the lens opposite an outer surface of the lens upon which the film may form.

The light emitter is preferably configured to emit light toward the lens such that the emitted light is incident upon or is directed toward the lens. The light sensor is preferably configured to detect and/or measure the intensity of light reflected from the lens. The amount and intensity of light reflected from the lens is dependent in part upon the formation (i.e., the presence or absence) of the film on the outer surface of the lens. The technical effects of the invention include the ability to directly detect the presence or absence of a film such as ice, snow, frost and insect residue on a surface without the need for visual and/or tactile inspection of such surfaces.

The apparatus may be useful in applications where the detection of frost contamination such as on a wind tunnel model is desirable for conditions where temperatures and pressure are at an extreme. In addition, the apparatus may be applied as a maintenance tool for in-service commercial airliners and other aircraft as well as for vehicles such as automobiles and missiles. Advantageously, the apparatus, in one embodiment, facilitates the ability to distinguish frozen contaminants (e.g., frost, snow, ice) from non-frozen contaminants (e.g., insect residue, dirt, debris) that may build up on a surface such as on an aircraft wing.

The apparatus comprises the photoreflective sensor in combination with the lens and may be mounted at strategic locations on the aircraft such as on an aircraft wing leading edge and on upper surfaces thereof where ice is known to form. The lens may form a protective cover in order to shield or seal the photoreflective sensor from the elements such as rain, ice and debris typically encountered by an aircraft during flight and during ground operations. The lens may be formed of any suitably durable material and is preferably of a transparent or semi-transparent nature. For example, the lens may be formed of any suitable glass or plastic material or other polymeric material.

The lens may further comprise a part of a structure or the lens may be integrated with the structure such as with the exterior mold line surface of an aircraft wing. The lens may optionally include a band pass filter which may be configured to pass light of a wavelength that is substantially similar to the bandwidth of wavelength of the emitted light. In this regard, the band pass filter may be a narrow band filter in order to prevent erroneous operation of the apparatus in conditions where sunlight is directly incident upon the lens from a direction opposite that of the emitted light.

The photoreflective sensor may further comprise a light sensor which is preferably configured to measure a variety of parameters of the reflected light including, but not limited to, intensity, amplitude and frequency. In addition, the light sensor may be configured to detect or measure light having an intensity that is greater than a predetermined value. In this regard, the photoreflective sensor may be operatively coupled to a suitable display device which may include a controller for comparing values of intensity or amount of light sensed by the light sensor as compared to predetermined values which may be programmed into the controller.

In a further embodiment, measurements of the intensity of the reflected light sensed by the light sensor may be transmitted to a computer to determine the existence of the film such as by comparison to film thickness values derived from testing or analysis. The data may be provided to cockpit flight crew and/or ground crew by a suitable warning device or a display to assist the crew in the determination as to whether to initiate deicing/anti-icing procedures.

The apparatus may optionally include any one of a variety of atmospheric sensors including, but not limited to, temperature sensors and sensors for measuring barometric pressure, relative humidity and dew point. As is known in the art, dew point is the temperature at which air may be cooled at a given barometric pressure in order for water vapor to condense into liquid which may then form as ice on an aircraft in flight.

In this regard, a dew point that is below the freezing temperature may result in the formation of frost by deposition on the aircraft surfaces such as the aircraft wing. Therefore, by measuring temperature and barometric pressure, the apparatus as disclosed herein may provide a tool for determining the likelihood of the formation of icing on the wings. In addition, the ability to determine the dew point may provide a tool for predicting the existence of certain in-flight weather parameters that would be valuable for safe operation of aircraft such as the altitude of cloud base above which the formation of ice may occur.

Data regarding atmospheric conditions (e.g., barometric pressure, relative humidity) may also be provided to a computer along with the intensity measurements of the reflected light to determine the existence of the film and to determine the nature of the film composition (i.e., frozen contaminants vs. non-frozen contaminants). Cockpit flight crew and/or ground crew may be provided with the data to assist in the determination as to whether to initiate deicing/anti-icing procedures or to provide a warning of excessively thick accumulations of non-frozen contaminants such as insect residue, dirt and other debris.

The features, functions and advantages that have been discussed can be achieved independently in various embodiments of the present invention or may be combined in yet other embodiments, further details of which can be seen with reference to the following description and drawings below.

BRIEF DESCRIPTION OF THE DRAWINGS

These and other features of the present invention will become apparent upon reference to the drawings wherein like numbers refer to like parts throughout and wherein.

DETAILED DESCRIPTION OF THE INVENTION

Figure 1:
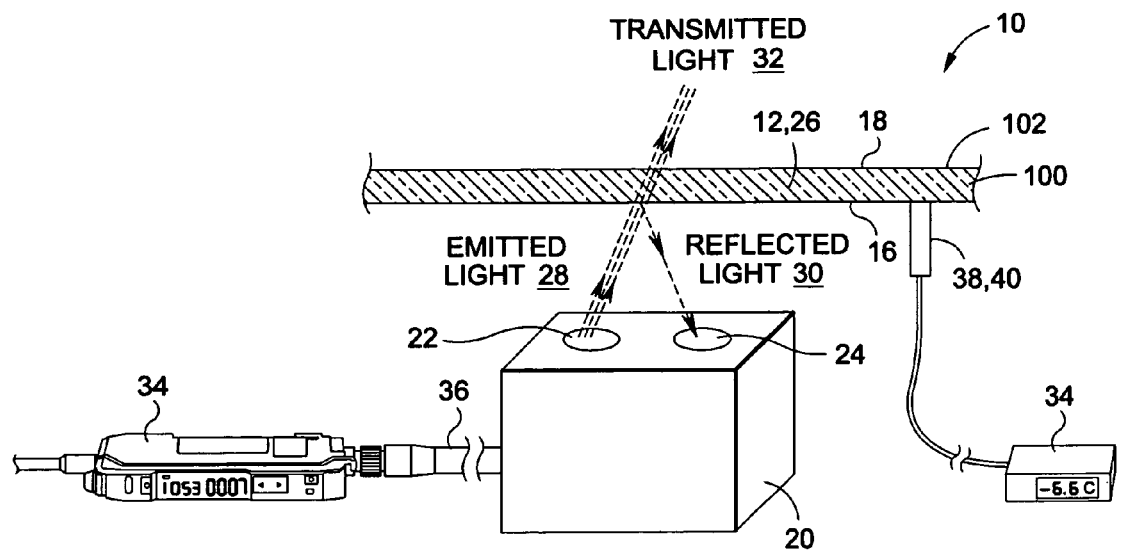
FIG. 1 is an illustration of one embodiment of an apparatus for detecting the presence or absence of a film on a surface and illustrating a photoreflective sensor disposed on an inner surface side of a lens.

Referring now to the drawings wherein the showings are for purposes of illustrating preferred and various embodiments of the present disclosure only and not for purposes of limiting the same, FIG. 1 is an illustration of an apparatus 10 for detecting the presence or absence of a film 14 on a surface 102. More particularly, the apparatus 10 as illustrated in certain embodiments described herein employs light to detect the presence of films such as frozen contaminants (i.e., frost, ice, snow) and various forms of debris (i.e., dirt, dust, insect residue).

In one embodiment, the apparatus 10 may comprise a photoreflective sensor 20 in combination with a lens 12 and/or filter 26 in order to monitor contamination that may build up as thin films on the surface 102 of the structure. The photoreflective sensor 20 may comprise a light emitter 22 and a light sensor 24 which are both preferably disposed in spaced relation to the lens 12 in order to allow for the light that is emitted by the light emitter 22 to be reflected back from the lens 12 towards the light sensor 24. In this regard, the photoreflective sensor 20 is adapted to detect and measure the amount of light reflected from the film.

Measurements of the amount or intensity of the reflected light 30 sensed by the photoreflective sensor 20 may be transmitted to a computer to compare the measured values to predetermined values corresponding to film 14 thicknesses that may be developed during testing or analytically. Flight crew may be alerted via a cockpit display or other suitable warning device of excessive film 14 thickness buildup and may request visual or tactile inspection of the aircraft 100 by ground crew prior to initiating deicing/anti-icing procedures or surface-cleaning procedures for non-frozen contamination.

Figure 2:
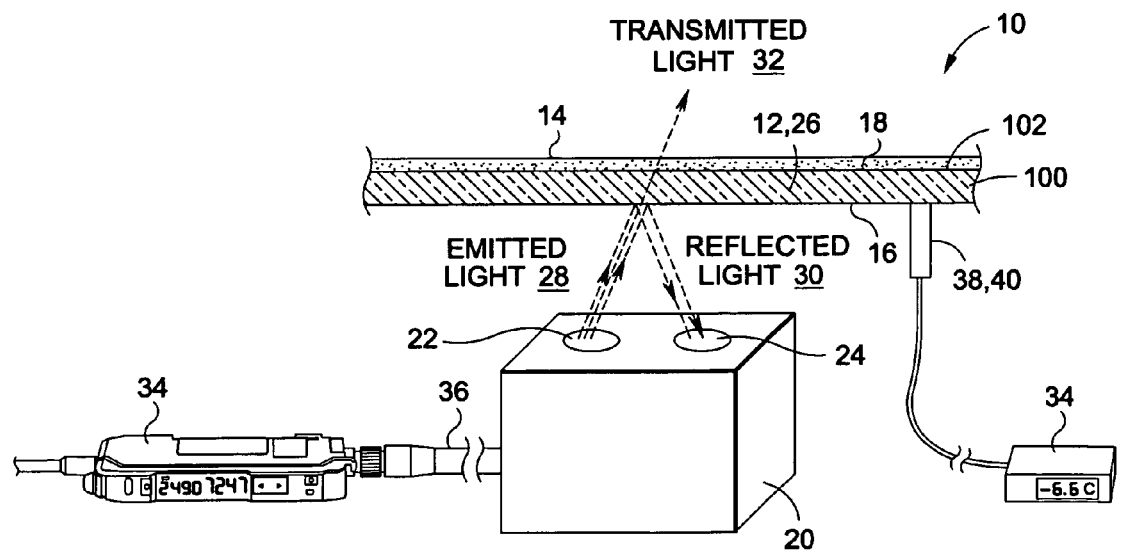
FIG. 2 is an illustration of the apparatus illustrated in FIG. 1 and further illustrating the deposition or accumulation of a film of frozen contaminants (i.e., snow, ice, frost) or debris (i.e., dust, dirt, dirt residue) and further illustrating the optional installation of a temperature sensor or atmospheric sensor on an inner or outer surface of the lens.

Referring to FIG. 2, the lens 12 may include an inner surface 16 and an outer surface 18. The outer surface 18 may be exposed to the environment or atmosphere while the inner surface 16 of the lens 12 may have the photoreflective sensor 20 disposed adjacent thereto. The apparatus 10 may optionally include an atmospheric sensor 40 such as a temperature sensor 38 for measuring a temperature of the lens 12 or for measuring other conditions of the atmosphere which may be conducive to the formation of frozen contaminants on the surface 102. In this regard, the optional inclusion of the atmospheric sensor 40 and/or temperature sensor 38 allows for determining and distinguishing the composition of the contamination and, more specifically, whether the contamination is a frozen composition such as ice, snow or frost or whether the contamination comprises a non-frozen composition such as dirt, dust, insect debris or deicing/anti-icing agents.

Measurements of atmospheric conditions (e.g., barometric pressure, relative humidity) may be provided to a computer along with intensity measurements of the reflected light 30 to determine the nature of the composition (i.e., frozen contaminants vs. non-frozen contaminants). Flight crew may be alerted via a suitable warning device of accumulations of frozen contaminants such as snow, ice or frost such that the appropriate deice-anti-icing procedures may be initiated. Likewise, a warning may be provided to flight crew/ground crew of excessive buildup of non-frozen contamination such that appropriate surface cleaning procedures may be initiated.

The lens 12 may comprise a semi-transparent or a transparent cover or protective shield which may seal and protect the photoreflective sensor 20 from the elements. Furthermore, the outer surface 18 of the lens 12 serves as the surface 102 against which the film 14 may form for detection and measurement by the photoreflective sensor 20. In one embodiment, the lens 12 may be disposed adjacent to or continuous with an exterior surface 102 of a vehicle 100 such as the outer mold line 102 surface of an aircraft wing 104. For example, the lens 12 may comprise a glass or plastic window mounted on or continuous with the outer mold line 102 surface of the aircraft such as on wing 104 leading edges, control surfaces and other areas of the aircraft where ice is known to form.

Figure 3:
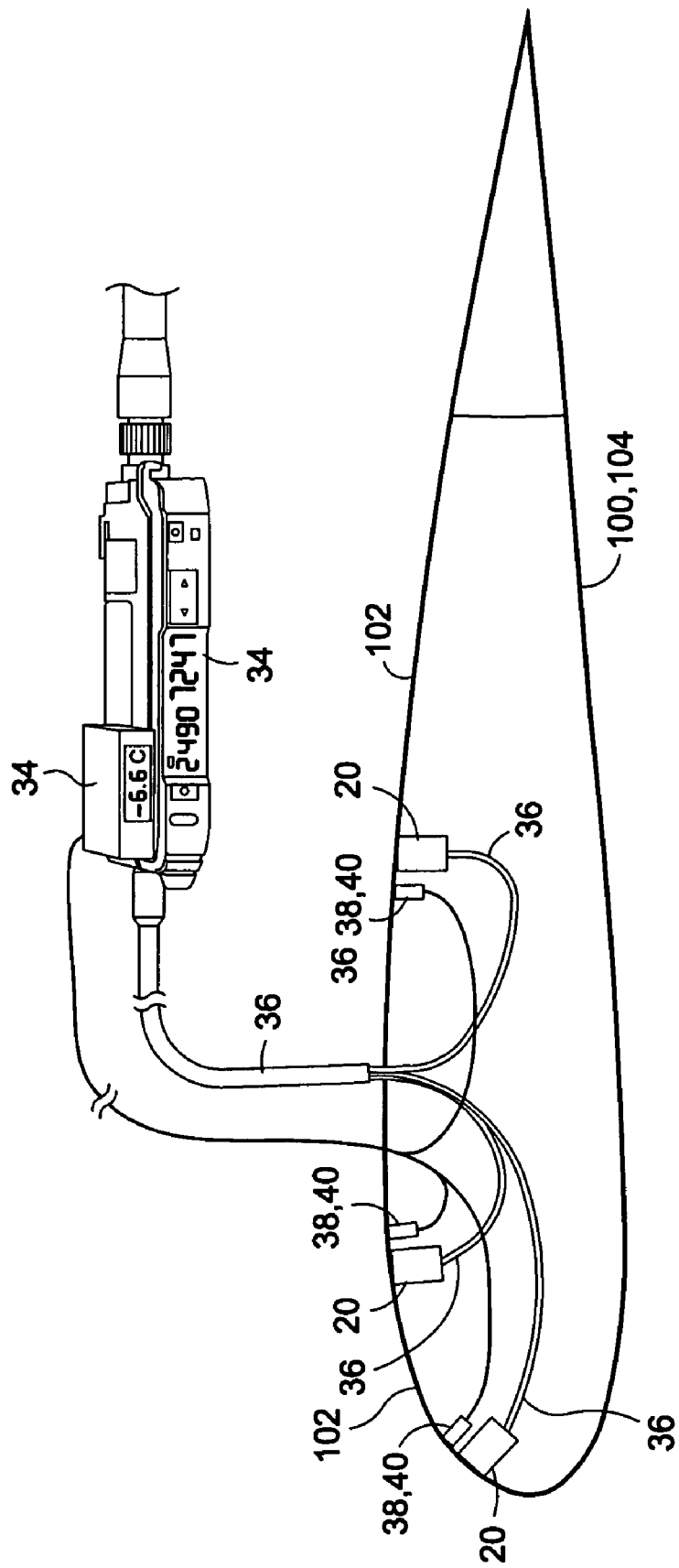
FIG. 3 is an illustration of the apparatus mounted at strategic locations on an aircraft wing and further illustrating a pair of display devices operatively coupled to the photoreflective sensors and to the atmospheric/temperature sensors.

Referring to FIG. 3, shown is an exemplary embodiment of one arrangement for installation of the apparatus disclosed herein and illustrating a set of photoreflective sensors 20 installed along the leading edge and extending along the upper surfaces of the wing 104 to approximate mid-chord. In one embodiment, the lens 12 may be mounted substantially flush or even with the outer mold line 102 surface of the aircraft wing 104 such that the aerodynamics thereof are undisturbed. As can be seen in FIGS. 1-3, the photoreflective sensors 20 are disposed within the wing 104 and are preferably mounted adjacent the lens 12 with the optional inclusion of temperature sensors 38 and/or atmospheric sensors 40 which may be mounted adjacent each one of the photoreflective sensors 20.

Referring to FIGS. 1 and 2, the lens 12 may be formed of any suitable material including, but not limited to, any polymeric material, glass, plastic, or any metallic or non-metallic material or combination thereof. However, it is also contemplated that the lens 12 may comprise part of the exterior surface or exterior skin of the structure to which the photoreflective sensor 20 is mounted. For example, the lens 12 may comprise a transparent or semi-transparent portion of a composite or polymeric wing structure. As was earlier mentioned, the lens 12 is preferably fabricated to be transparent or semi-transparent and preferably serves as a protective cover for the photoreflective sensor 20 against the elements such as ice, snow, rain and debris frequently encountered during ground and flight operations.

The photoreflective sensors 20 are preferably configured to include the light emitter 22 and the light sensor 24. The light emitter 22 is preferably disposed in spaced relation to the lens 12 and is configured to emit light toward the lens 12 such that the emitted light 28 is incident upon the lens 12. If the lens 12 is devoid of any type of film 14 contamination such as ice, snow, frost or debris such as insect residue, a majority of the transmitted light 32 will pass through the lens 12 as illustrated in FIG. 1 with a small portion of the reflected light 30 being reflected back at the angle of incidence into the light sensor 24. The light sensor 24 is configured to measure or detect light reflected back from the lens 12.

Referring to FIG. 2, shown is an illustration of the lens 12 having a film 14 of contamination disposed on the outer surface 18. As can be seen in FIG. 2, the film 14 creates a barrier against the transmitted light 32. Therefore, a larger portion of the emitted light 28 may be reflected back toward the light sensor 24 as compared to FIG. 1 where a majority of the emitted light 28 passes through the lens 12 as transmitted light 32. The photoreflective sensor 20 can detect and measure the intensity or amount of light that is reflected back from the lens 12 relative to the amount of light that is emitted by the light emitter 22.

Regarding the configuration of the light emitter 22 and the light sensor 24 of the photoreflective sensor 20, any suitable arrangement may be used in the apparatus 10 disclosed herein. For example, the photoreflective sensor 20 may be provided in any suitable size, shape and configuration and may be configured to emit light in any wavelength and frequency including light in a visible and non-visible spectrum. In this regard, the light emitter 22 may be configured as any variety of light sources including, but not limited to, a light emitting diode (LED), laser light, incandescent lamp, fluorescent lamp, infrared lamp and any other suitable light sources. Furthermore, the light emitter 22 may be configured to emit light in any intensity and in any color.

Likewise, the light sensor 24 may be configured in any suitable arrangement for detecting and measuring the amount and intensity of light reflected from the lens 12. For example, the light emitter 22 may be provided as a photoreflective sensor 20 or a photodetector. Furthermore, the light sensor 24 may be configured as a photo resistor for changing resistance according to light intensity, a photo-voltaic cell for producing voltage or current depending on the amount of illumination of reflected light 30, or as photo diodes, photo transistors, charged-coupled devices (CCD) and a variety of other sensor configurations.

The light sensor 24 is preferably configured to measure at least the intensity of the reflected light 30 but may further be configured to measure other parameters of the reflected light 30 including, but not limited to, wavelength, frequency, etc. The photoreflective sensor 20 may be further configured to compare the amount and/or intensity of the reflected light 30 to a predetermined value in order to determine the presence or absence of the film 14 on the lens 12. The light sensor 24 may also be configured to emit light within a variety of wavelength bands including, but not limited to, infrared, visible, and ultraviolet wavelengths.

Referring to FIG. 3, the photoreflective sensors 20 may be operatively coupled to any suitable display device 34 by means of a suitable conduit 36. In a preferable embodiment, the conduit 36 which couples the photoreflective sensors 20 to the display device 34 may be a fiber optic cable which provides a means by which the light beam may travel through a core of the fiber optic cable by bouncing off interior walls of the cable.

In an exemplary embodiment, the display device 34 may include a controller and is preferably of a configuration commercially available from Keyence Corporation of America, Woodcliff Lake, N.J. and designated as model number FS-V21RP. In a preferable embodiment, the fiber optic cable which operatively couples the display device 34 to the photoreflective sensor 20 may be that which is also commercially available from Keyence Corporation and which is designated as model number FU-67TZ.

Referring still to FIGS. 1-3, the apparatus 10 may also include the atmospheric sensors 40 such as the temperature sensor 38 configured for measuring the temperature of the lens 12 in order to determine the nature of the film 14 on the lens 12. For example, when the temperature sensor 38 detects that the temperature is at a point which is conducive to the formation of ice and the photoreflective sensor 20 detects that a film 14 has formed on the outer surface 18 of the lens 12, the apparatus 10 can determine that the contamination is that of frost or other frozen contaminants as distinguished from non-frozen contamination such as dirt, insect debris, deicing agents or anti-ice agents, etc.

In a further embodiment, the atmospheric sensor 40 may be configured to measure the barometric pressure and/or relative humidity in order to assess whether conditions are conducive for the formation of frost. For example, in conditions of high relative humidity, frost may form on surfaces during conditions where temperatures are at or below the dew point or frost point. By including such atmospheric sensors 40 in combination with the photoreflective sensor 20, it is possible to distinguish the nature of the contamination.

Furthermore, the arrangement of the apparatus 10 provides the ability to distinguish whether the film 14 is a liquid such as a rain, water, deicing agent or anti-icing agent as distinguished from solid contamination such as ice, frost, insect debris and dust. In this regard, the signal received at the display device 34 will fluctuate in response to movement of the liquid to indicate that the film 14 is water (i.e., droplets of rain) or trickling streams of deicing/anti-icing agent as opposed to a generally constant signal produced by light reflected from a solid or non-moving film such as ice.

The apparatus 10 may be mountable in a variety of applications and is not limited to aircraft. For example, the apparatus 10 may be mountable along or integrated with ground vehicles or any other structure or objects where contamination detection is desired. Alternatively, the apparatus 10 may be mounted in refrigeration units to detect and monitor frost buildup. In a further example, the apparatus 10 may be mounted in automobiles in order to determine or detect the existence of frost or fog and enable heating, ventilation and air conditioning (HVAC) systems to activate defrosting mechanisms to prevent fog buildup of windows in high humidity, low temperatures conditions.

Likewise, the apparatus 10 may be used as a maintenance tool for use on a variety of alternative vehicles such as missiles and other projectiles in order to detect frost contamination, insect residue and other debris buildup on exterior surfaces. For example, the apparatus 10 may be used to detect frost contamination on aircraft models in wind tunnel environments under extreme conditions of temperature and pressure.

For in-flight aircraft, the apparatus 10 may be employed to detect the formation of ice on aircraft wings 104 and control surfaces at an early stage such that the pilot may take evasive action to avoid further accumulations of ice which may compromise the safety of the aircraft. In this regard, early detection of ice formation on the wings 104 may allow the pilot to descend to a lower altitude where warmer temperatures prevent further buildup and allow for melting of existing ice formations.

In a further embodiment, the apparatus 10 may be configured to detect the rate of film 14 buildup by correlating the degree of the film 14 buildup to elapsed time. An increase in film 14 thickness may be indicated by an increase in the amount or intensity of reflected light 30 as measured by the light sensor 24. In this regard, a time history of film 14 thickness may be compared to elapsed time in order to assess a predicted film 14 thickness and determine whether further operation in the current environment poses a risk to the safety of the aircraft.

Figure 4:
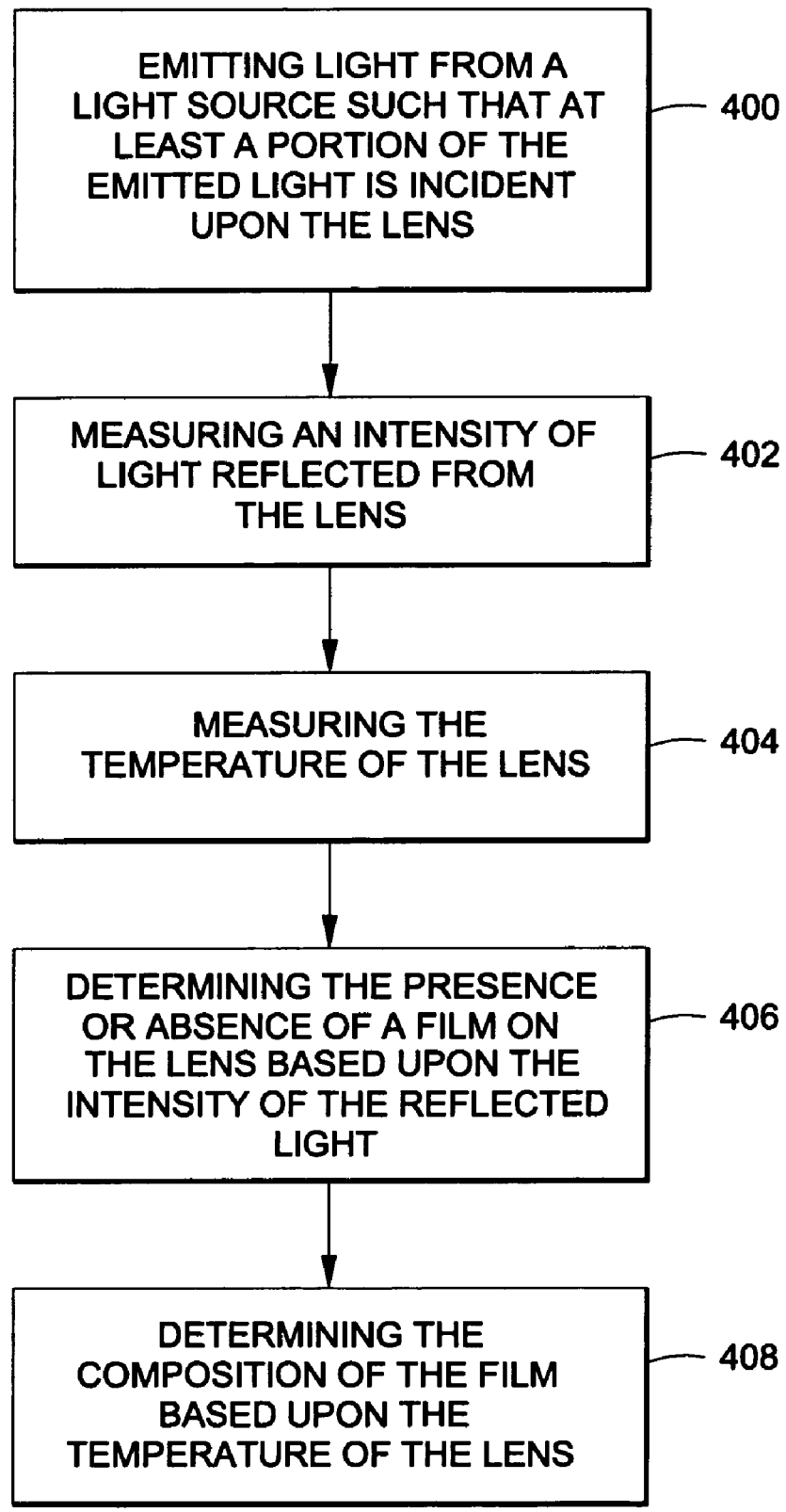
FIG. 4 illustrates an exemplary method of detecting the presence of the film on a surface.

Referring now to FIG. 4, shown is a flowchart illustrating an exemplary embodiment of a process for detecting the presence or absence of a film 14 on a surface 102 such as on a aircraft wing 104. As shown in FIG. 4, the process may include step 400 of emitting light from the light source such that at least a portion of the emitted light 28 is incident upon or is directed toward the lens 12. As was indicated above, the lens 12 may include the inner surface 16 and the outer surface 18. The outer surface 18 may be continuous with the outer mold line 102 surface of the aircraft wing 104.

The method may further comprise the step of receiving reflected light 30 at the light sensor 24 of the photoreflective sensor 20. In step 402, the photoreflective sensor 20 may be configured to measure the intensity or amount of light which is reflected from the lens 12. Measurements of the intensity of the light may be transmitted to a computer for comparison to predetermined values correlated to film 14 buildup. The process may further include step 406 of determining the existence or nonexistence of the film 14 as well as the thickness of the film 14 that has formed on the outer surface 18. Such data may be provided to flight crew and/or ground crew such that appropriate action may be initiated.

The method may comprise step 404 of measuring the temperature of the lens 12 such as the temperature of the outer surface 18. The method may further comprise step 408 of determining the composition of the film 14 based upon the temperature of the lens 12 and/or based upon the measurement of other atmospheric conditions such as barometric pressure or relative humidity of the atmosphere. Based upon the intensity of the reflected light 30 and the temperature of the lens 12 or other atmospheric conditions as compared to predetermined values, the composition of the film 14 on the outer surface 18 of the lens 12 may be determined and flight crew and/or ground crew may be alerted or such conditions may displayed on cockpit instrumentation.

In this regard, it may be determined whether the film 14 composition comprises frozen contamination such as ice, snow, frost or whether the film 14 comprises non-frozen contamination such as insect debris, dust, dirt, and other forms of non-frozen residue. The measurement of other atmospheric conditions such as barometric pressure or relative humidity may facilitate the determination of whether conditions are conducive to the formation of ice or frost. The existence of the film 14 or the absence thereof is determined based upon the intensity or the amount of light which is reflected from the lens 12.

The method may further comprise the step of sensing a change in any one of a variety of parameters of the reflected light 30 as compared to a baseline value. For example, the apparatus 10 may be operative to sense a change in frequency, amplitude and/or wavelength of the reflected light 30. The method may further comprise the step of detecting the rate of film 14 buildup by correlating film 14 thickness to elapsed time in order to generate a time history of the film 14 buildup in order to predict future film 14 thicknesses and determine whether measures must be taken to reduce such film 14 buildup. Such data may be provided to a flight computer and/or a cockpit warning device to alert flight crew of the need to take appropriate action.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. An apparatus for detection of a film on a surface, comprising:
   a lens having an inner surface;
   a light emitter configured to emit light toward the lens;
   a light sensor configured to measure an intensity of light reflected from the lens;
   a controller configured to compare values of intensity of the reflected light to predetermined values;
   a temperature sensor mounted on the inner surface of the lens for measuring a temperature of the lens;
   a sensor configured to measure barometric pressure and relative humidity; and
   a computer configured to determine the existence of the film based upon the intensity of the reflected light and the composition of the film based upon the temperature of the lens, the barometric pressure, and the relative humidity.

2. The apparatus of claim 1 wherein:
   the light emitter and the light sensor are disposed proximate the inner surface and being arranged in spaced relationship thereto.

3. The apparatus of claim 1 further comprising:
   a band pass filter configured to pass light having a wavelength falling within a wavelength band of the emitted light.

4. The apparatus of claim 1 wherein:
   the light emitter is configured as at least one of the following: light emitting diode (LED), laser, incandescent lamp, fluorescent lamp.

5. The apparatus of claim 1 wherein:
   the lens is configured to be semi-transparent to visible light.

6. The apparatus of claim 1 wherein:
   the lens is substantially flush with a surface of an aircraft.

7. The apparatus of claim 6 wherein:
   the aircraft surface is an outer mold line of a wing.

8. The apparatus of claim 7 wherein:
   the light emitter and the light sensor are disposed beneath the outer mold line.

9. The apparatus of claim 1 wherein the light sensor generates a signal produced by the reflected light, the apparatus further comprising:
   a display device coupled to the light sensor, the display device distinguishing liquid film from solid film based on fluctuations in the signal.

10. An aircraft, comprising:
    an apparatus for detection of a film on a surface, the apparatus including:
    a lens having an inner surface;
    a light emitter configured to emit light toward the lens;
    a light sensor configured to measure an intensity of light reflected from the lens;
    a controller configured to compare values of intensity of the reflected light to predetermined values; and
    a temperature sensor mounted on the inner surface of the lens for measuring a temperature of the lens;
    a sensor configured to measure barometric pressure and relative humidity; and
    a computer configured to determine the existence of the film based upon the intensity of the reflected light and the composition of the film based upon the temperature of the lens, the barometric pressure, and the relative humidity.

11. The aircraft of claim 10 further comprising:
    a band pass filter configured to pass light having a wavelength falling within a wavelength band of the emitted light.

12. The aircraft of claim 10 wherein:
    the lens is substantially flush with an outer mold line of a wing.

13. The aircraft of claim 10 further comprising:
    at least one wing having an outer mold line surface;
    wherein the light emitter and the light sensor are disposed beneath the outer mold line surface.

14. The apparatus of claim 13 wherein the lens is substantially flush with the outer mold line surface.

15. A method of detecting the presence of a film, comprising the steps of:
    emitting light from a light source such that at least a portion of the emitted light is incident upon the lens;
    measuring an intensity of light reflected from the lens;
    measuring barometric pressure and relative humidity;
    measuring the temperature of the lens using a sensor mounted on an inner surface of the lens;
    determining the existence of the film based upon the intensity of the reflected light; and
    determining the composition of the film based upon the temperature of the lens and the barometric pressure and relative humidity of the atmosphere.

16. The method of claim 15 further comprising the step of:
    sensing a change in the intensity of light reflected from the film in comparison to a predetermined value.

17. The method of claim 15 further comprising the step of:
    detecting a rate of film buildup by correlating the film thickness to elapsed time.

18. The method of claim 15 further comprising the step of:
    producing a signal based on the reflected light; and
    distinguishing liquid film from solid film based on fluctuations in the signal.

* * * * *